(12) United States Patent
Snow

(10) Patent No.: US 9,707,386 B2
(45) Date of Patent: Jul. 18, 2017

(54) VALVED CONNECTOR

(75) Inventor: Jeremy W. Snow, South Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 13/495,608

(22) Filed: Jun. 13, 2012

(65) Prior Publication Data

US 2013/0150795 A1    Jun. 13, 2013

Related U.S. Application Data

(63) Continuation of application No. 12/701,995, filed on Feb. 8, 2010, now Pat. No. 8,206,375.

(60) Provisional application No. 61/150,751, filed on Feb. 7, 2009, provisional application No. 61/286,649, filed on Dec. 15, 2009.

(51) Int. Cl.
*A61M 39/00* (2006.01)
*A61M 39/06* (2006.01)
*A61M 39/02* (2006.01)

(52) U.S. Cl.
CPC ........ *A61M 39/06* (2013.01); *A61M 39/0247* (2013.01); *A61M 39/0606* (2013.01); *A61M 2039/062* (2013.01); *A61M 2039/066* (2013.01); *A61M 2039/0633* (2013.01)

(58) Field of Classification Search
CPC .... A61M 2039/062; A61M 2039/0633; A61M 2039/066; A61M 39/0247; A61M 39/06; A61M 39/0606
USPC .......................... 604/174, 246–256, 533–538
See application file for complete search history.

(56) References Cited

U.S. PATENT DOCUMENTS

| | | | |
|---|---|---|---|
| 1,029,819 | A | 6/1912 | Nylander |
| 3,162,470 | A | 12/1964 | Owens et al. |
| D213,957 | S | 4/1969 | Myerly |
| 4,143,853 | A | 3/1979 | Abramson |

(Continued)

FOREIGN PATENT DOCUMENTS

| JP | S59131364 | 7/1984 |
|---|---|---|
| JP | S6121107 | 5/1986 |

(Continued)

OTHER PUBLICATIONS

Office Action dated Sep. 30, 2009 for U.S. Appl. No. 12/151,889.

(Continued)

*Primary Examiner* — Imani Hayman
(74) *Attorney, Agent, or Firm* — Stoel Rives LLP

(57) ABSTRACT

A valved connector configured to control the leakage of bodily fluid from within a patient. The valved connector including a seal positioned within a lumen of the body of the valved connector. The distal end of the valved connector is adapted to permit access to, or coupling of an apparatus. A proximal end is adapted to be threadably coupled to a secondary device. The needless connector valve being configured to be openable by a dilator or post of an apparatus which is connected to the proximal end of the needleless connector. In the event that a luer coupler or other secondary apparatus is not available, a needle, cannula, trocar, or other instrument can be threaded through the main lumen of the valved connector opening the valve and allowing the passage of fluid directly through the needle, trocar, cannula, or other instrument.

17 Claims, 14 Drawing Sheets

(56) References Cited

U.S. PATENT DOCUMENTS

| | | |
|---|---|---|
| 4,387,879 A | 6/1983 | Tauschinski |
| 4,665,959 A | 5/1987 | Takagi |
| 4,844,512 A | 7/1989 | Gahwiler |
| D33,260 S | 9/1990 | Kelly |
| D313,067 S | 12/1990 | Kotake et al. |
| 5,062,836 A | 11/1991 | Wendell |
| 5,064,416 A | 11/1991 | Newgard et al. |
| 5,300,034 A | 4/1994 | Behnke et al. |
| 5,312,363 A | 5/1994 | Ryan et al. |
| 5,456,675 A | 10/1995 | Wolbring et al. |
| 5,464,400 A | 11/1995 | Collins |
| 5,584,808 A | 12/1996 | Healy |
| D387,146 S | 12/1997 | Morrison |
| 5,989,233 A | 11/1999 | Yoon |
| 6,113,068 A | 9/2000 | Ryan |
| D441,436 S | 5/2001 | Chao |
| 6,287,280 B1 | 9/2001 | Lampropoulos et al. |
| 6,482,188 B1 | 11/2002 | Rogers et al. |
| D476,957 S | 7/2003 | Chudoba et al. |
| 6,595,981 B2 | 7/2003 | Huet |
| D482,761 S | 11/2003 | Gotoh et al. |
| 6,651,956 B2 | 11/2003 | Miller |
| 6,669,681 B2 | 12/2003 | Jepson et al. |
| D495,050 S | 8/2004 | Guala |
| 6,971,390 B1 | 12/2005 | Vasek et al. |
| 7,140,592 B2 | 11/2006 | Phillips |
| 7,226,433 B2 * | 6/2007 | Bonnette ............... A61B 17/22 604/164.01 |
| D569,955 S | 5/2008 | Chen |
| D570,457 S | 6/2008 | Brown |
| 7,434,846 B2 | 10/2008 | Baumgartner |
| D583,026 S | 12/2008 | Dirneder |
| 7,497,484 B2 | 3/2009 | Ziman |
| D594,938 S | 6/2009 | Dirneder |
| D627,038 S | 11/2010 | Yu |
| D627,039 S | 11/2010 | Yu |
| D645,547 S | 9/2011 | Lombardi et al. |
| D648,008 S | 11/2011 | Percoco et al. |
| D649,228 S | 11/2011 | Drenth |
| D674,058 S | 1/2013 | Yu |
| 8,377,039 B2 * | 2/2013 | Utterberg et al. ............ 604/533 |
| D716,916 S | 11/2014 | Snow |
| 2002/0062106 A1 | 5/2002 | Chu et al. |
| 2003/0141477 A1 | 7/2003 | Miller |
| 2004/0143219 A1 | 7/2004 | Lee et al. |
| 2005/0261630 A1 | 11/2005 | Mottola |
| 2007/0043334 A1 | 2/2007 | Guala |
| 2008/0018105 A1 | 1/2008 | Le Bars |
| 2008/0082082 A1 | 4/2008 | Carlyon et al. |
| 2008/0140055 A1 | 6/2008 | Shirley |
| 2008/0287921 A1 | 11/2008 | Bennett |
| 2009/0270941 A1 * | 10/2009 | Mokelke ............ A61M 25/104 607/37 |
| 2010/0022951 A1 * | 1/2010 | Ferrera et al. ............... 604/103 |
| 2010/0179484 A1 * | 7/2010 | Carrez ............ A61M 25/09041 604/187 |
| 2010/0217208 A1 | 8/2010 | Snow |

FOREIGN PATENT DOCUMENTS

| | | |
|---|---|---|
| JP | 2825663 | 11/1998 |
| JP | 3142630 | 5/2008 |
| JP | 4116785 | 7/2008 |
| WO | 2007044878 | 4/2007 |
| WO | 2007050755 | 5/2007 |
| WO | 2008042285 | 4/2008 |
| WO | WO2010/091356 | 8/2010 |

OTHER PUBLICATIONS

International Search Report and Written Opinion dated Apr. 20, 2010 for PCT/US2010/23491.
Office Action dated Jun. 23, 2010 for U.S. Appl. No. 12/151,889.
Office Action dated Dec. 27, 2010 for U.S. Appl. No. 12/151,889.
Notice of Allowance dated Jun. 3, 2011 for U.S. Appl. No. 12/151,889.
Notice of Allowance dated Apr. 9, 2012 for U.S. Appl. No. 12/701,995.
Office Action dated Dec. 22, 2011 for U.S. Appl. No. 12/701,995.
Office Action dated Jul. 15, 2011 for U.S. Appl. No. 12/701,995.
U.S. Appl. No. 29/435,009, filed Oct. 18, 2012, Snow.
Restriction Requirement dated May 15, 2014 for U.S. Appl. No. 29/435,009.
Notice of Allowance dated Jul. 18, 2014 for U.S. Appl. No. 29/435,009.
European Search Report dated May 23, 2017 for EP10739232.6.

* cited by examiner

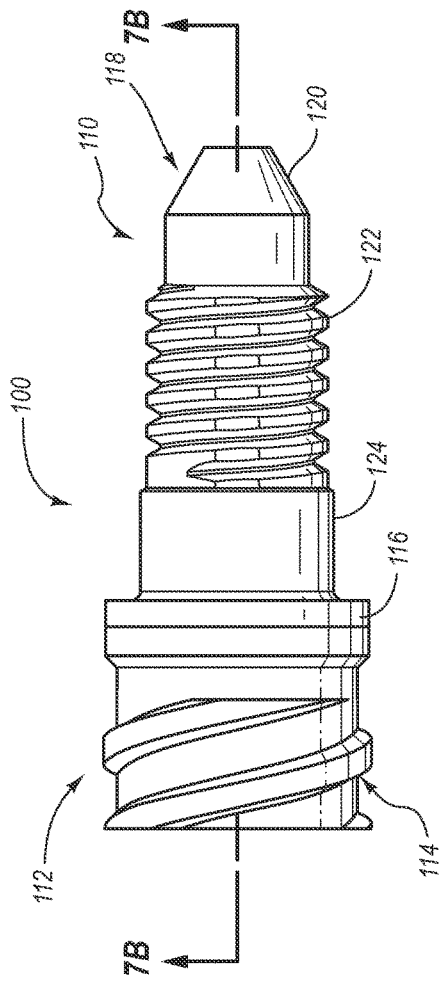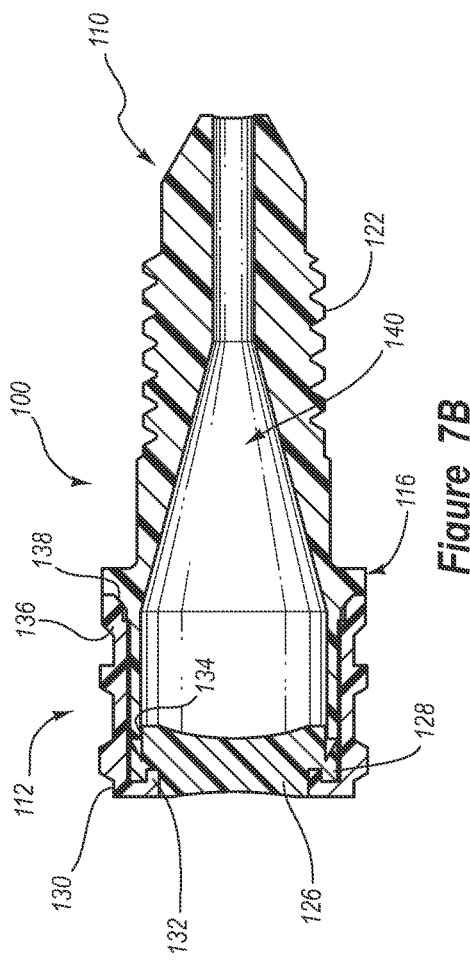

VALVED CONNECTOR

CROSS REFERENCE TO RELATED APPLICATIONS

This application is a continuation of co-pending U.S. patent application Ser. No. 12/701,995 filed on Feb. 8, 2010 which, in turn, claims the benefit of U.S. Provisional Patent Application No. 61/150,751, filed on Feb. 7, 2009, and U.S. Provisional Patent Application No. 61/286,649, filed on Dec. 15, 2009, all of which are herein incorporated by reference in their entireties.

BACKGROUND OF THE INVENTION

Field of the Invention

The present invention relates to a valved connector which is configured to be placed in fluid communication with a volume of fluid. In more particular, the present invention relates to a valved connector, which is adapted to allow the passage of fluids from a patient to the external environment utilizing one or both of a threaded connector and a needle or cannula positioned within the lumen of the valved connector.

Relevant Technology

Valved connectors have been utilized to control the passage of fluid. Oftentimes in modern medicine, a volume of fluid will collect within the tissue or other location within a patient's body. Additionally, at times it is desirable to control the flow of blood, or urine when a particular patient access site is accessed. In such situations, a practitioner can use a connector which has an incorporated valve to limit the undesired flow of fluids from the patient at inopportune times.

One of the deficiencies of currently utilized connectors is that most connectors either allow the unrestricted flow of fluids, or alternatively the connector is cumbersome to use. When a volume of bodily fluid within a patient is accessed, some valved connectors will allow the largely unrestricted passage of fluid until the proximal end of the connector is coupled to a secondary device. Alternatively, some connectors require complicated and cumbersome movement of the stop cock handle or other secondary apparatus to control the passage of fluid through the connector.

Valved connectors are typically configured such that only one of a variety of different types of mechanisms can be utilized to permit flow of fluid. For example, one such apparatus may utilize only a stop cock to control the passage of fluid through the connector. A secondary device, may only allow a needle, trocar or other elongate instrument to permit the passage of fluid. Yet another apparatus may allow a luer-type connector to actuate the passage of fluid. Additionally, valved connectors are typically not configured to allow the introduction of the guide wire through the connector. In the event that a guide wire is positioned within the patient, a connector cannot be threaded over the guide wire. As a result, fluid communication with the volume of bodily fluid is not permitted until the guide wire has been removed and a secondary apparatus is utilized.

Such valved connector apparatus are often cumbersome, non-intuitive, and complicated to use, limiting the types and variety of surgical or interventional procedures with which such connectors can be utilized. For example, in some instances, once the connector is in fluid communication with the volume of bodily fluid, a stop cock is turned to an open or closed position as desired to control the passage of fluid through a side tubing. Subsequently, a practitioner can insert a needle directly through the lumen of the connector to permit the passage of fluids out of the needle. However, once the needle has been positioned through the apparatus, the stop cock handle can no longer be turned without removal of the needle or other instrument. Other valved connector may permit the opening of the valve of the connector utilizing a luer fitting with a secondary device. However, such valved connectors are not configured to allow the use of a needle to open the valve in the event that a luer connector is not desired or is unavailable.

BRIEF DESCRIPTION OF THE DRAWINGS

FIG. 7A is a side perspective view of a valved connector according to one illustrative aspect of the present invention.

FIG. 7B is a cross-sectional view of a valved connector according to one illustrative aspect of the present invention.

BRIEF SUMMARY OF THE INVENTION

Figure 1A:
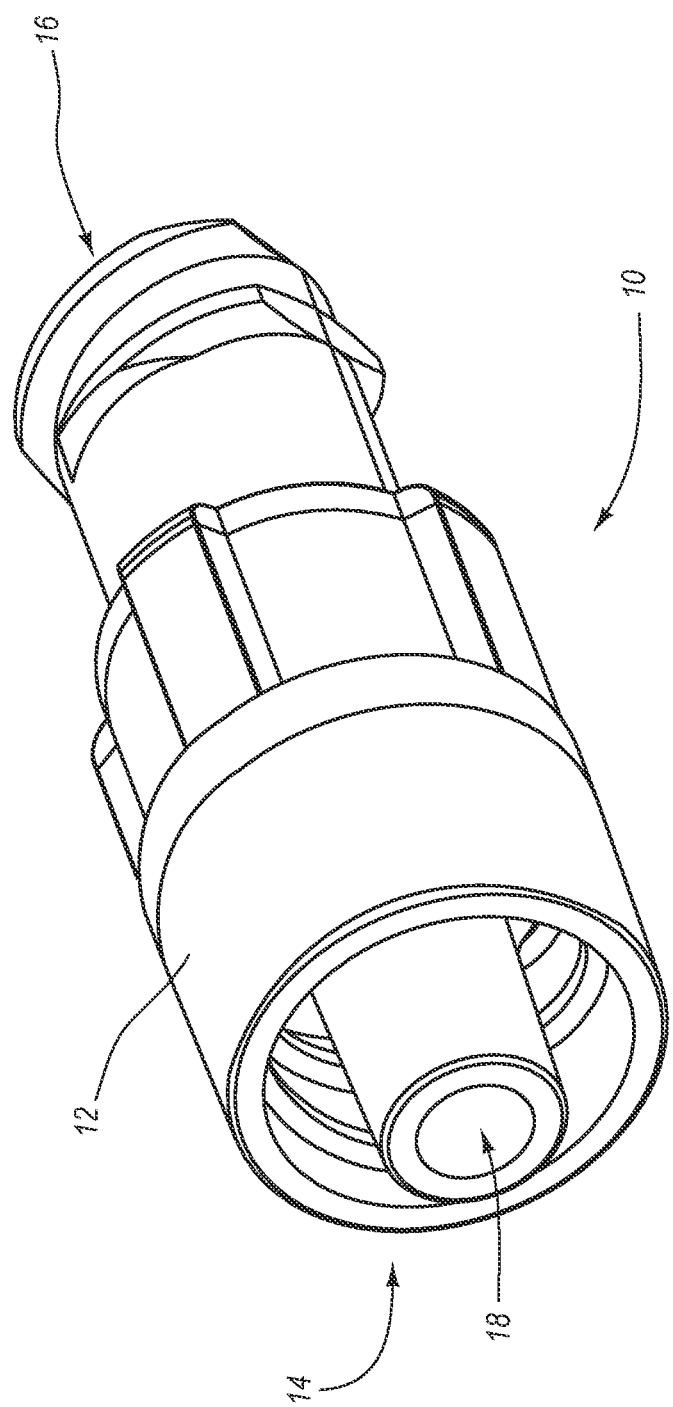
FIG. 1A is a front perspective view of a valved connector.

The present apparatus is directed to a valved connector. The valved connector is adapted to selectively permit the passage of fluid. The valved connector can be coupled with a catheter or other secondary access device. In another embodiment, the catheter tip or micropuncture-type apparatus is integrally coupled to the valved connector with the valved connector being positioned in the hub of the assembly.

According to one embodiment of the present invention, the valved connector includes a seal positioned within a lumen of the body of the valved connector. The distal end of the valved connector is adapted to permit access to, or coupling of a secondary apparatus, which is placed in fluid communication with the volume of fluid. A proximal end is adapted to be threadably coupled to a secondary device. When the proximal end is threadably coupled or otherwise engaged by the secondary device, a seal engagement apparatus positioned within the proximal end of the valved connector engages the valve allowing the passage of fluid through the lumen of the valved connector. In the event that a luer coupler or other secondary apparatus is not available, a needle, cannula, trocar, or other instrument can be threaded through the main lumen of the valved connector opening the valve and allowing the passage of fluid directly through the needle, trocar, cannula, or other instrument.

Additional aspects and advantages will be apparent from the following detailed description of preferred embodiments, which proceeds with reference to the accompanying drawings.

DETAILED DESCRIPTION

The present apparatus is directed to a valved connector. The valved connector is adapted to selectively permit the passage of fluid. The valved connector can be coupled with a catheter or other secondary access device. In another embodiment, the catheter tip or micropuncture-type apparatus is integrally coupled to the valved connector with the valved connector being positioned in the hub of the assembly.

According to one embodiment of the present invention, the valved connector includes a seal positioned within a lumen of the body of the valved connector. The distal end of the valved connector is adapted to permit access to, or coupling of a secondary apparatus. A proximal end is adapted to be threadably coupled to a secondary device. When the proximal end is threadably coupled or otherwise engaged by the secondary device, a seal engagement apparatus positioned within the proximal end of the valved connector engages the valve allowing the passage of fluid through the lumen of the valved connector. In the event that a luer coupler or other secondary apparatus is not available, a needle, cannula, trocar, or other instrument can be threaded through the main lumen of the valved connector opening the valve and allowing the passage of fluid directly through the needle, trocar, cannula, or other instrument.

FIG. 1 is a perspective view of a valved connector 10 according to one embodiment of the present invention. In the illustrated embodiment, valved connector 10 is adapted to be utilized with a catheter or other instrument which is positioned within an access site. In some embodiments, the valve apparatus is adapted to allow desired instruments or other procedures to be performed while maintaining hemostasis.

In the illustrated embodiment, valved connector 10 comprises a body 12, a female connector 16, a male connector 14, and a main lumen 18. In the illustrated embodiment, male connector 14 is positioned on the distal end of valved connector 10. In the embodiment, male connector 14, is connected to a catheter, or other access device inserted into the patient. Main lumen 18 is through body 12 allowing passage of fluid from the distal end of valved connector 10 to the proximal end of valved connector 10. In the illustrated embodiment, a female connector 16 is positioned on the proximal end of the valved connector 10. Female connector 16 is adapted to be connected with a threaded coupler of a secondary device which is to be connected to valved connector 10. Such secondary device will typically include a post which extends into the main lumen on the proximal end of valved connector 10. The post of the secondary device is adapted to engage a seal engagement apparatus which selectively opens the seal to permit the passage of fluids when the secondary device is coupled to valved connector 10.

Valved connector 10 is also adapted to allow a needle, cannula, or other implement to be passed through main lumen 18. The configuration of the seal engagement apparatus (not shown) and valve (not shown) allows not only the passage of the instrument, but also the passage of fluid through the needle. The configuration permits the passage of fluid from the distal end of valved connector 10 to the proximal end of valved connector 10.

Figure 1B:
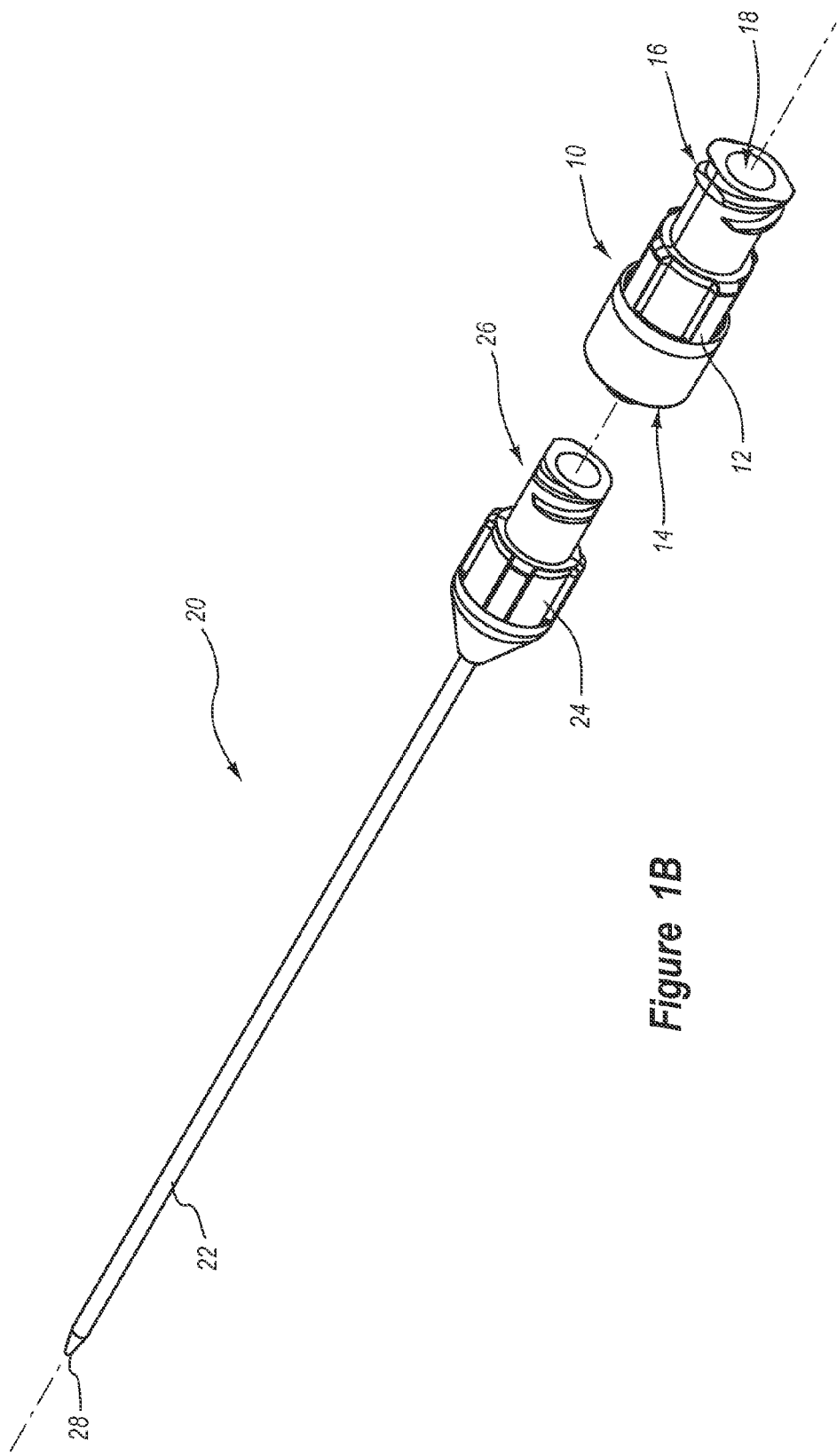
FIG. 1B is a front perspective view of a valved connector illustrating an access apparatus to which the valved connector can be utilized.

FIG. 1B is a perspective view of valved connector 10 and an access apparatus 20 to be utilized in connection with valved connector 10. In the illustrated embodiment, valved connector 10 can be secured to access apparatus either before or after the access procedure in which a distal end of access apparatus 20 is positioned within the patient. In the illustrated embodiment, access apparatus 20 comprises a catheter 22, a hub 24, and a female luer connector 26. Female luer connector 26 is threadably coupled to male connector 14 of valved connector 10. In a typical procedure, once access apparatus 20 is secured to valved connector 10, catheter 22 is positioned in fluid communication with the main lumen 18 of valved connector 10.

As will be appreciated by those skilled in the art, a variety of types and configurations of access apparatus can be utilized in connection with valved connector 10. For example, in one embodiment, valved connector 10 is secured to an access apparatus not having a threaded connector. In another embodiment, valved connector 10 is secured to a catheter, tubing, or other apparatus. In yet another embodiment, valved connector 10 is adapted to be secured to an apparatus that is not directly in fluid communication with the volume of fluid, but is instead connected to a secondary apparatus. In yet another embodiment, the valved connector is utilized to control the flow of fluid from one location to another location. For example, valved connector can be utilized with an infusate bag or medical tubing which is not in communication with a patient's body.

Figure 1C:
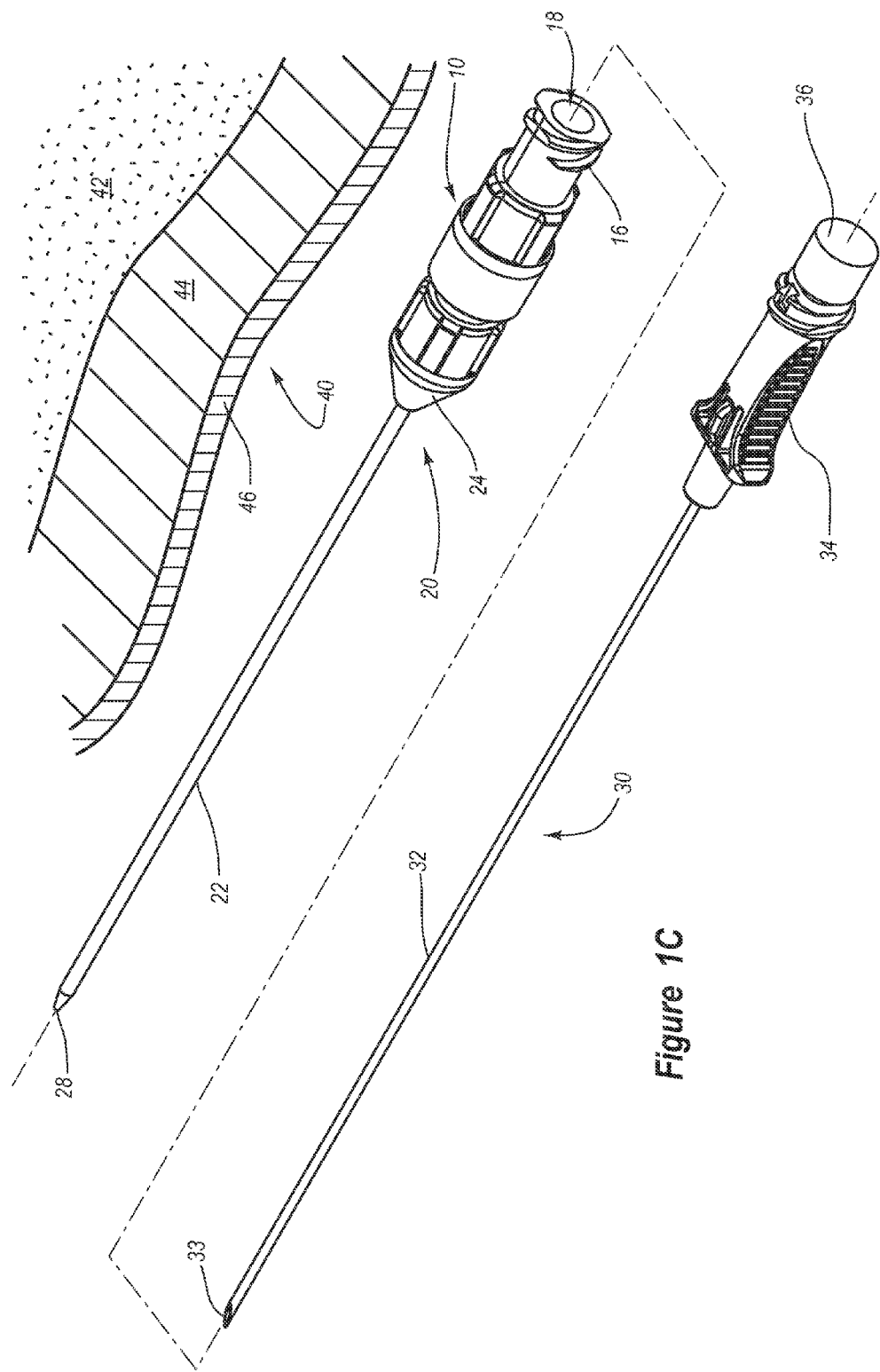
FIG. 1C is a front perspective view of a valved connector illustrating coupling of the valved connector to the access apparatus of FIG. 1B and a needle apparatus.

FIG. 1C is a perspective view of valved connector 10, depicting securement of valved connector 10 to access apparatus 20. In the illustrated embodiment, a needle apparatus 30 is shown. Needle apparatus 30 can be utilized to provide additional stiffness to catheter 22 during an insertion procedure. In the illustrated embodiment, a patient 40 is depicted. Patient 40 has a volume of fluid 42 positioned within the patient's body, which is to be accessed and/or drained from the patient. In the illustrated embodiment, patient tissue 44 and skin 46 are depicted in connection with patient 40.

Needle 30 is adapted to be threaded from the proximal end of valved connector 10. A needle tip 33 is introduced into main lumen 18 at the portion of main lumen 18 associated with female connector 16. Needle tip 33 is advanced such that it passes through body 12 of valved connector and into hub 24 of access apparatus 20. In this manner, needle cannula 32 is positioned through body 12 of valved connector such that needle cannula 32 is threaded through the valve positioned within body 12 of valved connector. The needle 30 is further advanced until needle tip 33 is positioned adjacent a catheter tip 28. According to one embodiment of the present invention, the length of needle cannula 32 is configured such that hub 34 of needle 30 is positioned adjacent female connector 16 of valved connector 10. In this manner, needle tip 33 is positioned exactly adjacent catheter tip 28 providing the sufficient rigidity and stiffness to catheter tip 28 along the entire length of catheter 22 such that catheter tip 28. In this manner, catheter tip 28 can be advanced into the volume of fluid 42 within patient 40. In the illustrated embodiment, a lumen 36 of needle 30 is depicted. Lumen 36 is adapted to run the entire length of needle 30 such that it runs from needle tip 33, through the length of needle cannula 32 and to the proximal end of hub 34.

As will be appreciated by those skilled in the art, a variety of types and configurations of access apparatus can be utilized without departing from the scope and spirit of the present invention. For example, in one embodiment, catheter 22 comprises a stiffened material which does not need a needle apparatus to be advanced to the desired position within the patient's tissue. In another embodiment, the needle is first inserted into the patient's tissue and then a catheter is advanced subsequently to the desired location within the patient's tissue. According to another embodiment, the valved connector is connected directly to the access apparatus once it has already been positioned within the patient.

Figure 1D:
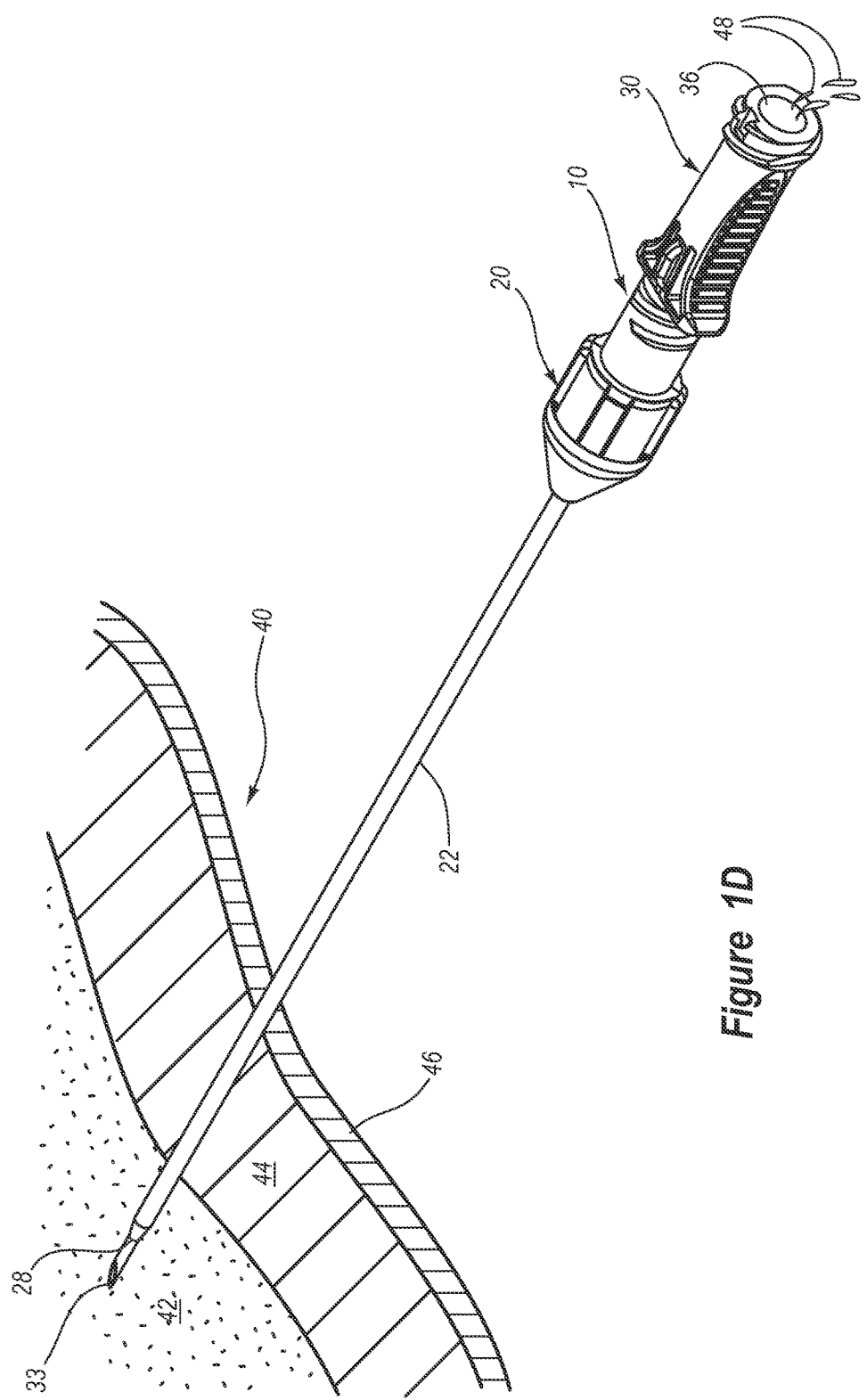
FIG. 1D is a front perspective view of a valved connector illustrating coupling of the valved connector to the access apparatus of FIG. 1B and to the needle apparatus of FIG. 1C and insertion of the access device into a patient.

FIG. 1D illustrates valved connector 10 once it has been positioned within the volume of fluid 42 within a patient 40. In the illustrated embodiment, needle tip 33 and catheter tip 28 have been advanced through the patient's skin 46, through the patient tissue 44, and into volume of fluid 42. In this manner, a direct fluid path is provided through access apparatus 20 and into valved connector 10.

In the illustrated embodiment, needle 30 provides a direct fluid path through the middle of the valve provided in connection with valved connector 10. As a result, when needle tip 33 and catheter tip 28 are positioned within the volume of fluid, fluid 48 from the volume of fluid 42 pass along the length of catheter 22, through access apparatus hub 24, along the length of valved connector 10, and out through the proximal end of lumen 36 of needle apparatus 30.

Figure 1E:
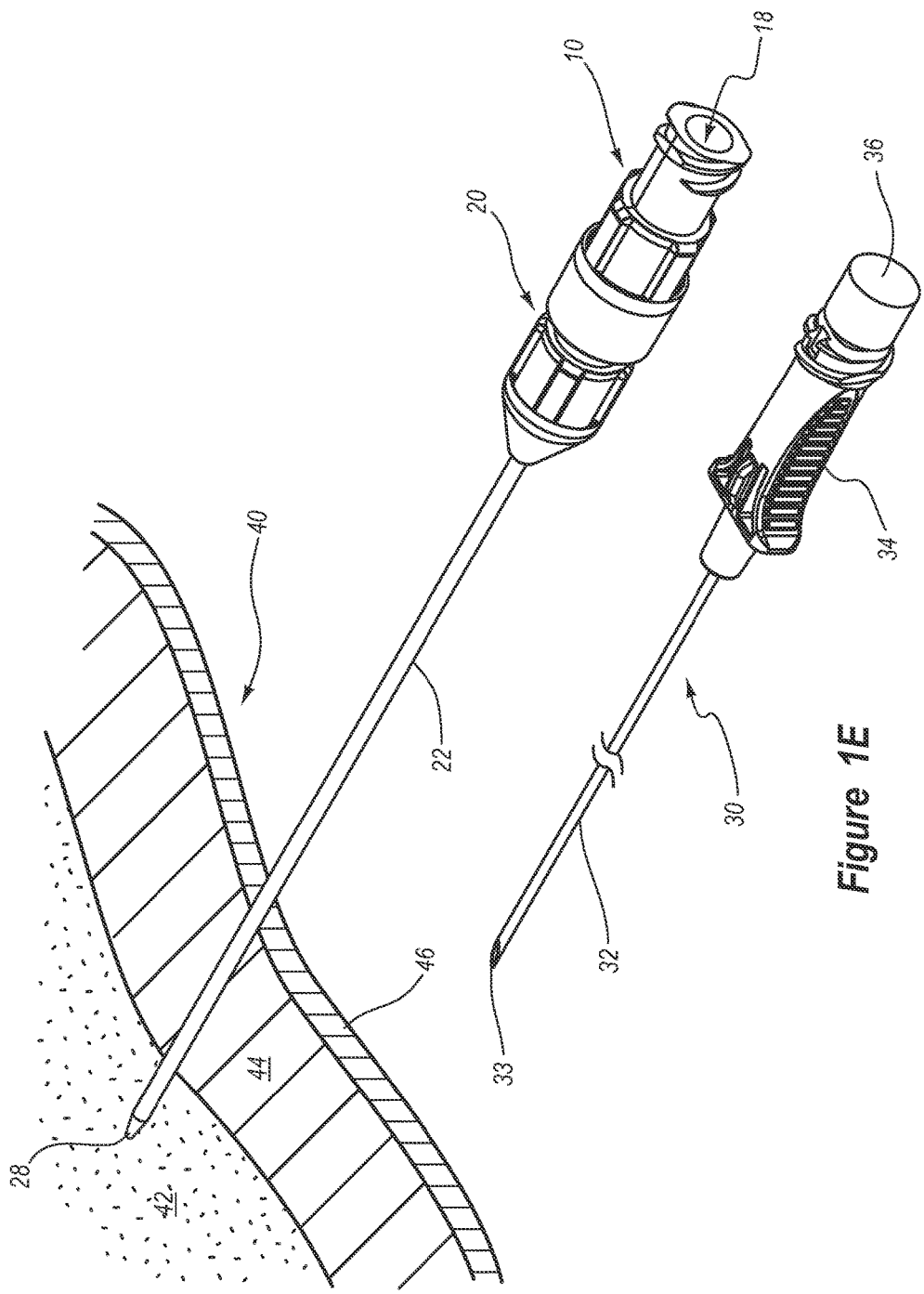
FIG. 1E is a front perspective view of a valved connector illustrating an access device positioned within a patient.

FIG. 1E illustrates valved connector 10 after needle apparatus 30 has been removed from valved connector 10 and access apparatus 20. When needle apparatus 30 has been removed from valved connector 10, catheter tip 28 remains positioned within the volume of fluid 42 within the patient 40. The valve associated with valved connector 10 prevents the passage of fluid out the proximal end of main lumen 18. As a result, while access apparatus 20 remains in a desired position such that the catheter tip 28 is positioned in the volume of fluid, undesired leakage of the fluid from access apparatus and valved connector 10 is limited. In this manner, other aspects of a procedure can be performed without the ongoing loss of fluid.

In one embodiment, a guide wire can be threaded through valved connector 10, access apparatus 20, and into the volume of fluid. A secondary apparatus can be advanced to a desired position within the patient at a subsequent portion of the procedure. For example, the valved connector and access apparatus may be removed once the volume of fluid has been drained. Subsequently, a catheter or interventional apparatus could be advanced to the location of the volume of fluid. According to another embodiment, access apparatus 20 is positioned within the patient's vasculature, and valved connector 10 prevents or minimizes the leakage of blood or fluid from the patient's vasculature. In this embodiment, a guide wire or other instrument can be advanced through valved connector while hemostasis is maintained.

Figure 1F:
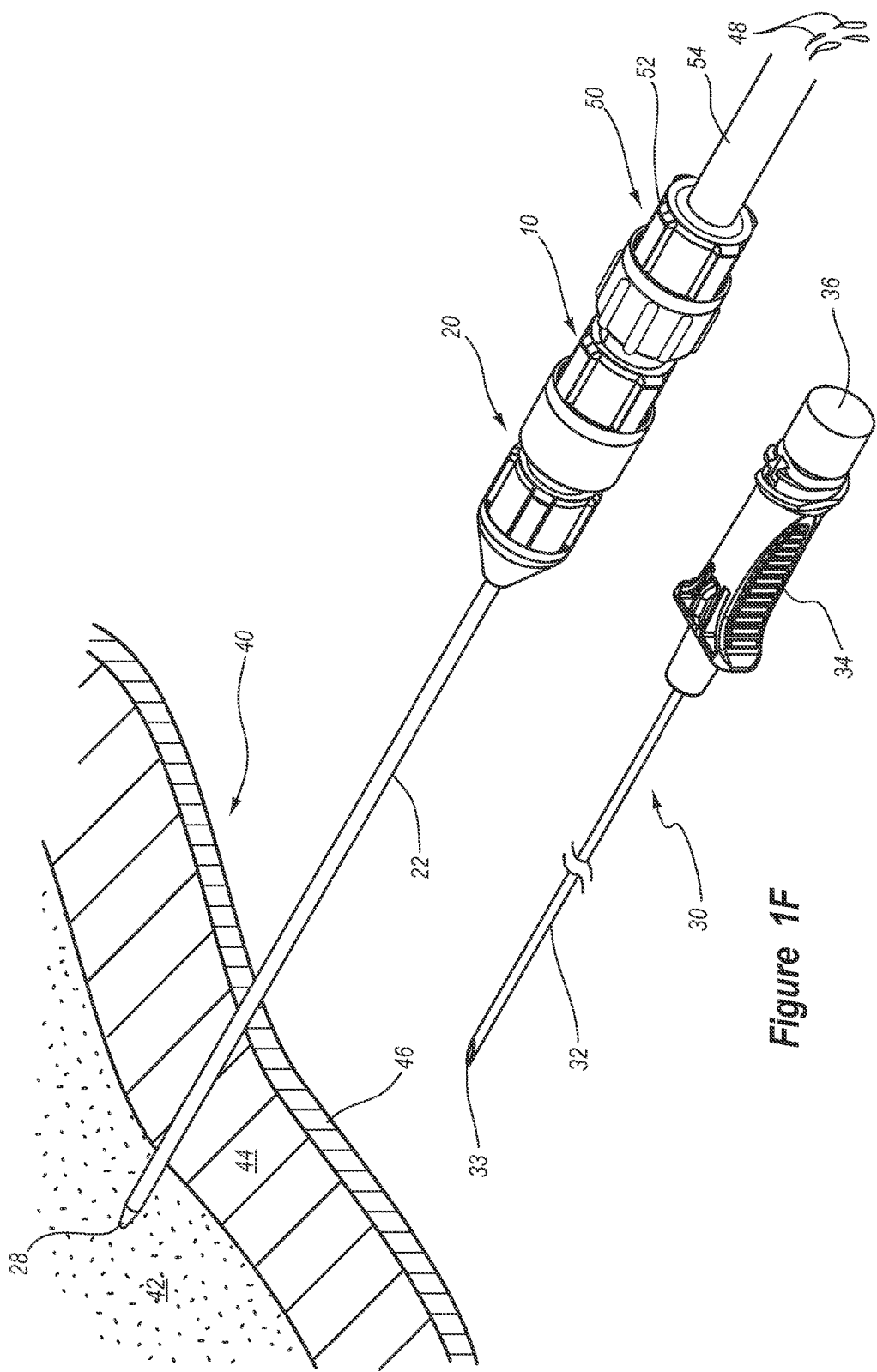
FIG. 1F is a front perspective view of a valved connector illustrating an access device positioned in a patient and a drainage apparatus coupled to the valved connector.

FIG. 1F is a perspective view of valved connector 10 and access apparatus 20 in which catheter tip 28 is positioned within a volume of fluid and a drainage apparatus 50 is connected to the proximal end of valved connector 10. In the illustrated embodiment, catheter tip 28 remains positioned within the volume of fluid 42 positioned within patient 40. A drainage apparatus 50 is connected to the proximal end of valved connector 10. Drainage apparatus 50 includes a luer connector 52 which is threadably coupled to the female connector 16 (see FIG. 1E) positioned on the proximal end of valved connector 10. When luer coupler is connected to the distal end of valved connector 10, the valve positioned within valved connector 10 is automatically opened and fluid is allowed to pass through valved connector and into drainage apparatus 50. In the illustrated embodiment, tubing 54 is connected to luer connector 52. Tubing 54 passes the fluid which is issuing from valved connector 10 to a secondary location. In the illustrated embodiment, tubing 54 is depicted as terminating to show the manner in which fluid can pass through and from tubing 54. In one embodiment, tubing 54 may be positioned over a tray or receptacle for receiving the bodily fluid. In another embodiment, tubing 54 may be connected to a bag or other receptacle for containing the fluid as it is drained or flows from the patient. In yet another embodiment, tubing 54 may be connected to a hemostasis valve or other apparatus to provide desired functionality, depending upon the requirements of the procedure being performed.

As will be appreciated by those skilled in the art, a variety of types of mechanisms can be utilized without departing from the scope and spirit of the present invention. For example, in one embodiment, a connector that is not threaded is secured to the distal end of the valved connector. In another embodiment, both the proximal and distal ends of the valved connector have the same type of securement configuration. For example, in one embodiment, both ends have a female connector. In another embodiment, both ends have a male connector. In another embodiment, both ends are adapted to include a compression or other fitting which does not require threads. In yet another embodiment, other known connection or securement type configurations can be utilized without departing from the scope and spirit of the present invention.

Figure 2:
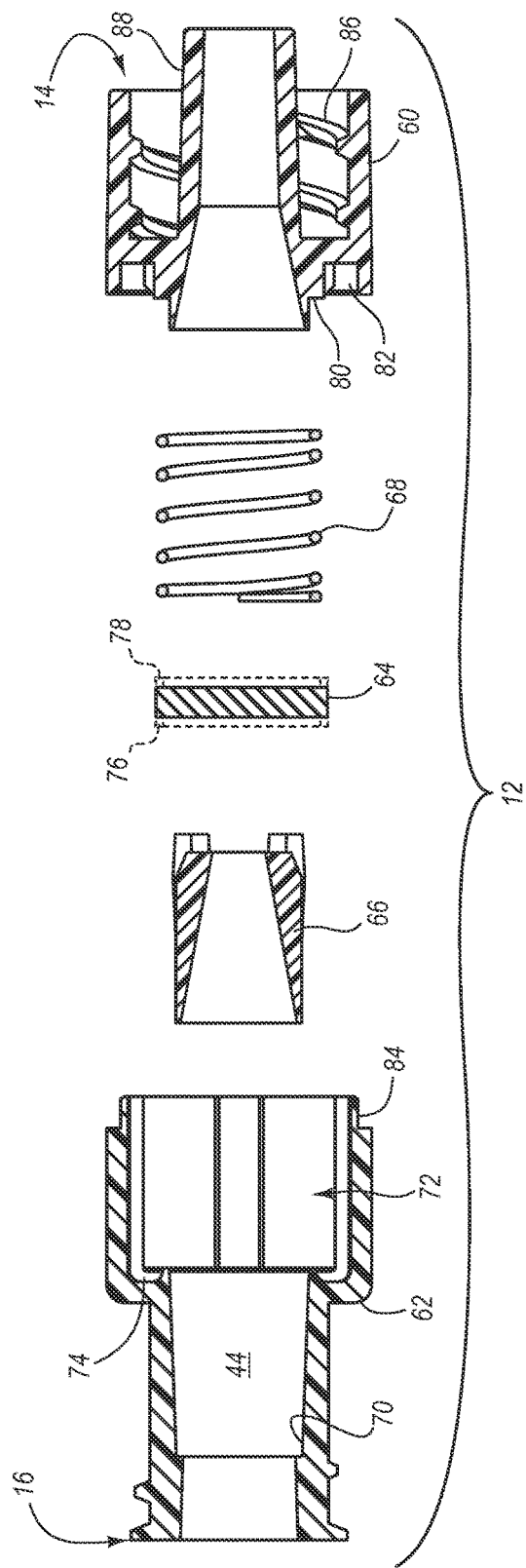
FIG. 2 is an partial exploded component view of the valved connector of FIG. 1A.

FIG. 2 is a perspective view of the valved connector according to one embodiment of the present invention. In the illustrated embodiment, valved connector 10 includes a distal body component 60, and a proximal body component 62. Additionally, valved connector 10 includes a seal 64, a seal engagement apparatus 66, and a spring 68. Distal body component 60 is associated with male connector 14. Proximal body component 62 is associated with female connector 16 and the proximal end of valved connector 10. In the illustrated embodiment, distal body component 60 includes a seal engagement apparatus receiving channel 70. In one embodiment, seal engagement apparatus receiving channel 70 has a conical design which permits axial movement of seal engagement apparatus 66. Distal body component 60 also includes a seal chamber 72. Seal chamber 72 is adapted to receive seal 64. Additionally, a spring 68 is adapted to be positioned between seal 64 and distal body component 60. Spring 68 facilitates the desired engagement of seal 64 with seal chamber 72. In the illustrated embodiment, seal chamber 72 includes a sealing channel 74. Sealing channel 74 receives a proximal sealing flange 76 of seal 64. In this manner, the pressure applied by spring 68 on seal 64 causes the desired engagement between proximal sealing flange 76 and sealing channel 74. In this manner, when seal engagement apparatus 66 is not engaged by a secondary mechanism, spring 68 can maintain desired sealing between seal 64 and seal chamber 72. When seal engagement apparatus is positioned within channel 70 and seal 64 is positioned within seal chamber 72, spring 68 is positioned between seal 64 and distal body component 60. Distal body component 60 includes a spring engagement post 80. Spring engagement post is sized such that the outer diameter of the spring engagement post 80 can be positioned within the inner diameter of spring 68. In this manner, the desired alignment of spring 68 relative to spring engagement post 80 is maintained. Once seal engagement apparatus 66, seal 64, and spring 68 have been positioned relative to distal body component 60 and proximal body component 62, distal body component 60 can be secured relative to proximal body component 62. Distal body component 60 includes an engagement void 82. Proximal body component 62 includes an engagement member 84. When distal body component 60 and proximal body component 62 are secured together, engagement member 84 is positioned within engagement void 82 facilitating desired coupling of distal body component 60 to proximal body component 62. In this manner, the internal components of valved connector including seal 64, seal engagement apparatus 66, and spring 68 are positioned in their desired location to facilitate desired operability of the components of valved connector 10.

In the illustrated embodiment, seal 64 includes a distal sealing flange 78. Distal sealing flange 78 facilitates the desired positioning of spring 68 relative to seal 64. In this manner, when seal 64 is displaced axially by the engagement of seal engagement apparatus 66, a uniform and desired amount of compression is provided by spring 68 to return seal 64 to its desired position within seal chamber 72 when such axial forces are no longer exerted by seal engagement apparatus on seal 64.

As will be appreciated by those skilled in the art, a variety of types and configurations of valved connector components can be provided without departing from the scope and spirit of the present invention. For example, in one embodiment, the body of valved connector is provided as a single component, rather than as first and second components. In another embodiment, the valve body is provided in a clam shell fitting, rather than as proximal and distal ends. In yet another embodiment, the body of valved connector is adapted such that the internal components can be inserted within or through the proximal or distal ends of the valved connector body. A retainment flange or other secondary apparatus is positioned to secure the components in their desired position.

Figure 3A:
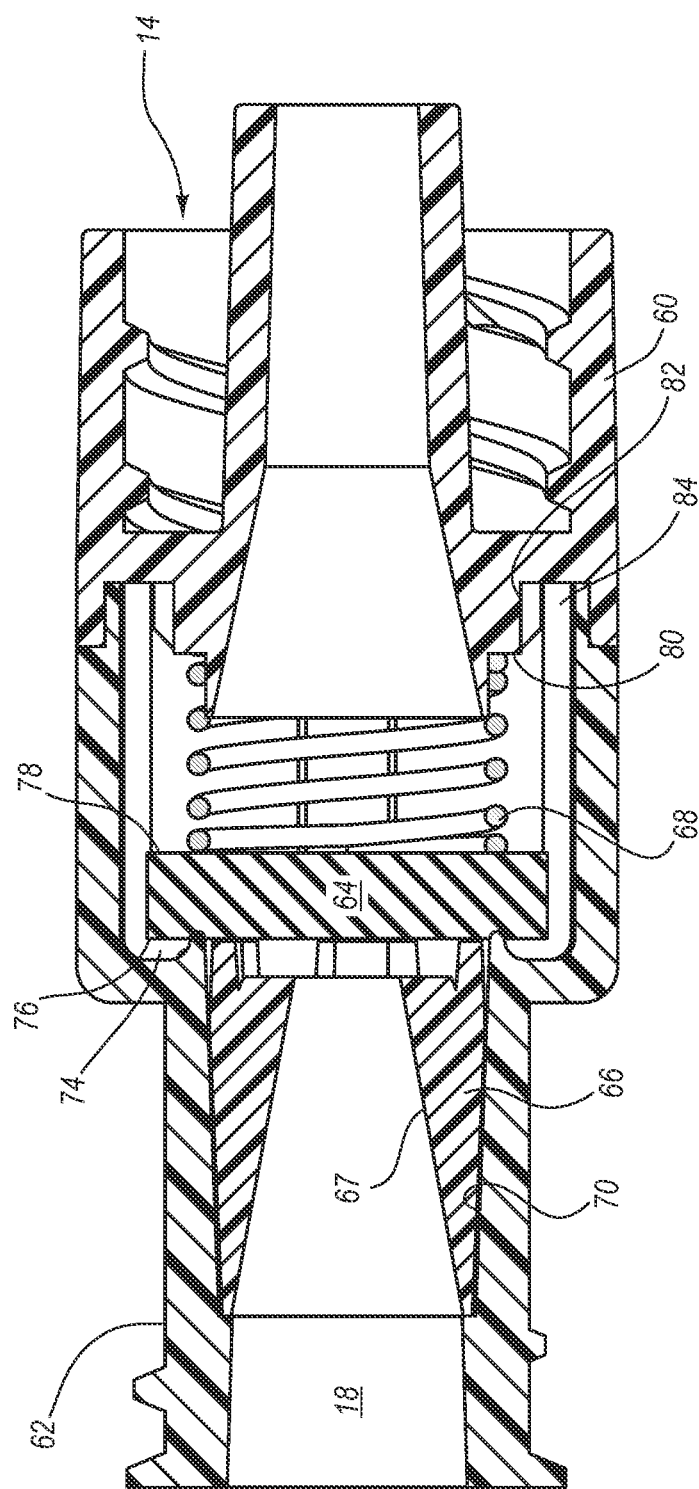
FIGS. 3A and 3B are cross-sectional views of the valved connector illustrating the juxtaposition of the internal components of the valved connector of FIG. 1B.
Figure 3B:
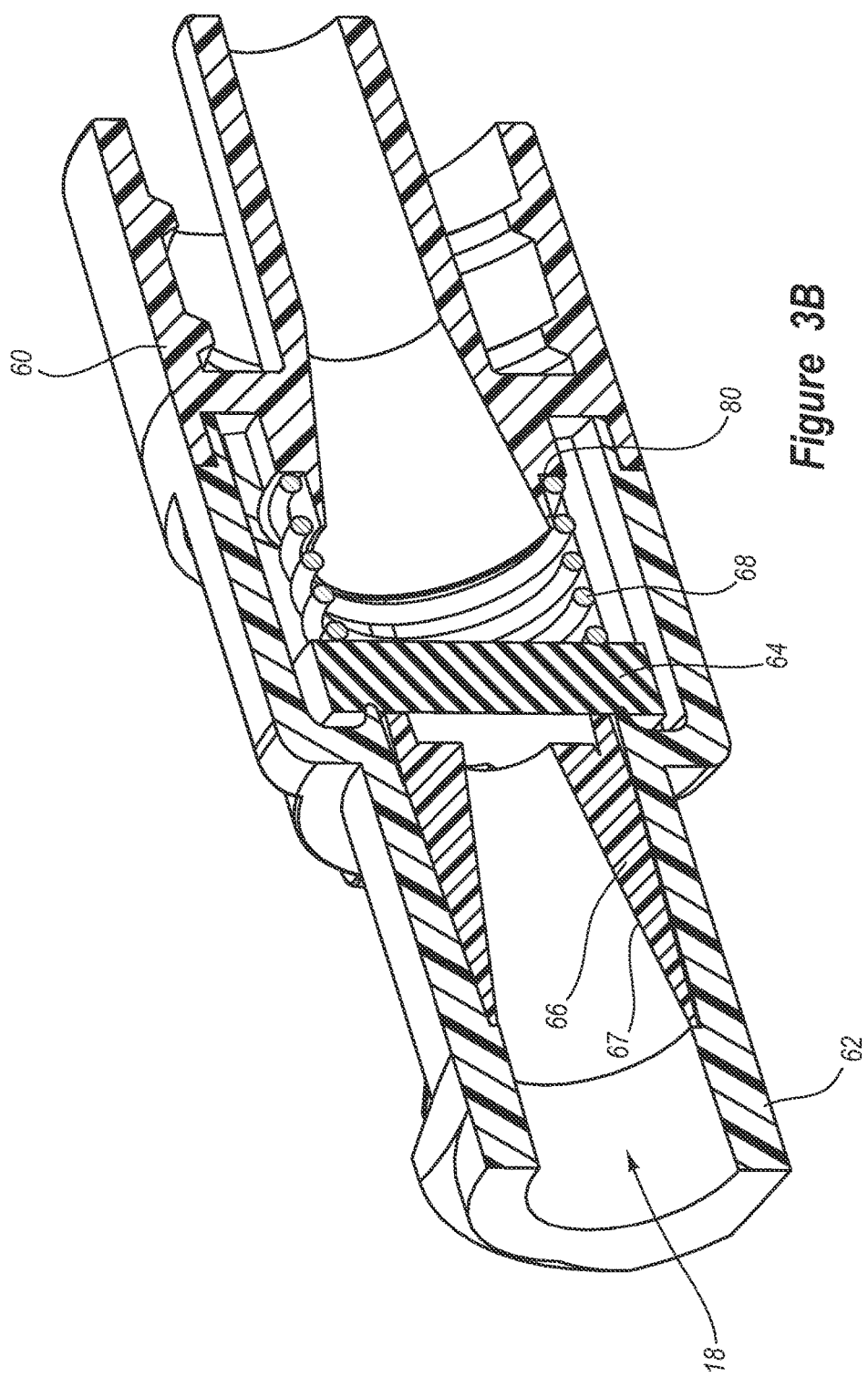

FIGS. 3A and 3B are cross-sectional view of valved connector 10 according to one embodiment of the present invention. In the illustrated embodiment, the positioning of the internal components of valved connector 10 can be seen. In the illustrated embodiment, seal 64 is positioned between the proximal and distal ends of valved connector 10. Seal engagement apparatus 66 is positioned between the proximal end of valved connector 10 and the seal 64. Spring 68 is positioned between the distal end of the valved connector 10 and the seal 64. In other words, the seal engagement apparatus 66 is positioned between the end of the valved connector 10. Spring 68 is positioned on the portion of the valved connector 10 opposite the end into which an apparatus is inserted such that the valve 64 is positioned between the spring and the end of the valved connector 10 into which a drainage apparatus is inserted.

Seal engagement apparatus 66 is positioned within seal engagement apparatus receiving channel 70. Channel 70 includes a flange at its proximal most position, which prevents further axial movement of seal engagement apparatus 66 in a proximal direction. In the illustrated embodiment, the distal end of seal engagement apparatus 66 is positioned adjacent seal 64. Seal 64 is positioned within seal chamber 72. Seal 64 is positioned such that the outer periphery of seal 64 is positioned proximal to the proximal sealing flange 76 and is in abutment with a contact surface at the distal most extremity of seal engagement apparatus receiving channel 70. Additionally, proximal sealing flange 76 is positioned within sealing channel 74.

Spring 68 is positioned between seal 64 and distal body component 60. In particular, the proximal portion of spring 68 is positioned such that the outside diameter of spring 68 is retained within distal sealing flange 78. The distal portion of spring 68 is positioned around spring engagement post 80 effectively retaining the angular orientation of spring 68 relative to seal 64. Spring 68 is sized such that a predetermined amount of tension is exerted against seal 64 retaining the desired engagement between seal 64 and the internal topography of seal chamber 72. In this manner, when a fluid column is positioned within the distal portion of main lumen 18, seal 64 prevents passage of the fluid from the distal portion of main lumen 18 to the proximal portion of main lumen 18.

FIG. 3B illustrates a perspective cross-sectional view of valved connector 10 illustrating the juxtaposition of seal engagement apparatus 66, seal 64, spring 68, distal body component 60, and proximal body component 62.

In the illustrated embodiment, in the event that a column of fluid is positioned within the distal portion of main lumen 18, the axial movement of seal 64 disrupts the sealing engagement between seal 64 and the internal profile of proximal body component 62. In this manner, when apparatus 50 is secured to valved connector 10, fluid can pass around the other periphery of seal 64 even though no component of apparatus 50 is directly in contact with seal 64. In other words, a secondary component, in this case, seal engagement apparatus, passes the axial force provided by apparatus. Opening the seal 64 and permitting the passage of fluids from the distal portion of valved connector 10 to the proximal portion of valved connector 10 and into apparatus 50. As will be appreciated by those skilled in the art, a variety of types and configurations of apparatus 50, which exert indirect forces on seal, can be utilized without departing from the scope and spirit of the present invention. For example, in one embodiment, the apparatus connected to valved connector has a threaded coupling with valved connector. In another embodiment, a non-threaded fitting is provided. In another embodiment, a user can selectively apply or remove forces relative to the seal engagement apparatus to open and close the seal, even without requiring movement or separation and reconnection of the drainage apparatus. In yet another embodiment, the axial forces exerted on seal are provided directly from the drainage apparatus rather than utilizing an intermediary seal engagement apparatus.

Figure 4:
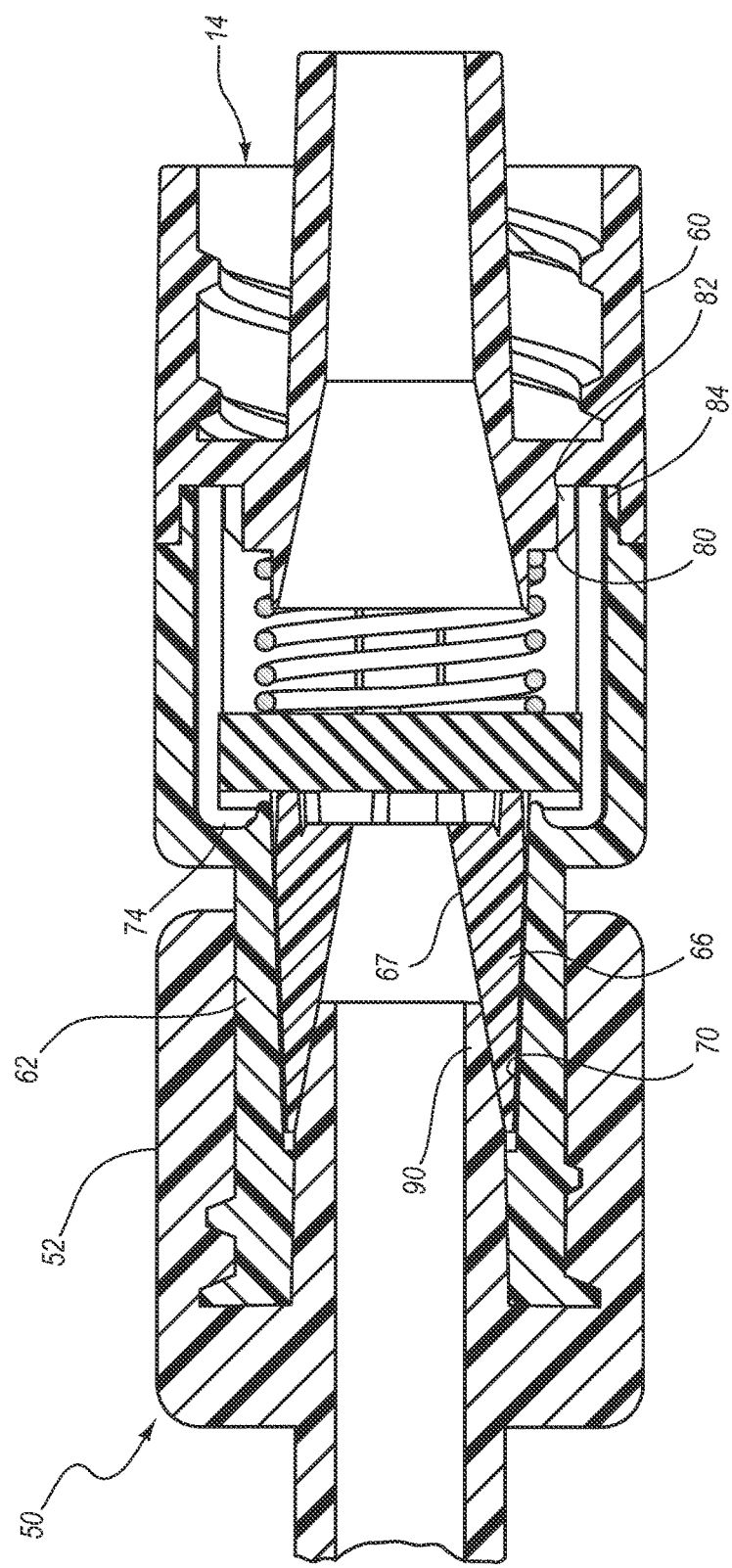
FIG. 4 is a cross-sectional side view of the valved connector illustrating the manner in which a seal engagement apparatus can be utilized to open the seal of the valved connector.

FIG. 4 is a cross-sectional view of valved connector 10. In the illustrated embodiment, a drainage apparatus 50 is provided in connection with the distal end of valved connector 10. Female connector 16 is secured to a male connecting portion of luer connector 52. Additionally, a post 90 has been positioned within the proximal portion of main lumen 18. In the illustrated embodiment, the distal portion of post 90 has been advanced such that it engages the tapered surface 67 of seal engagement apparatus 66.

In the illustrated embodiment, seal engagement apparatus 66 has a tapered surface 67. Tapered surface 67 provides a conical engagement surface which can engage a post of a secondary apparatus which is threaded through the proximal portion of main lumen 18. If the apparatus which is threaded through the proximal portion of main lumen 18 has a sufficient outside diameter, the distal portion of such apparatus will engage the wall of tapered surface 67 and provide a desired amount of axial force on tapered surface 67. In this manner, once a desired threshold force is provided, axial displacement of seal engagement apparatus is effectuated. In this manner, the forces exerted on tapered surface 67 are sufficient to overcome the tensile forces provided by spring 68 resulting in axial or lateral movement of seal 64. In this manner, desired sealing between seal 64 and seal chamber 72 are broken and fluids can pass around the outer periphery of seal 64. Passage of fluids around the outer periphery of seal 64 permits the passage of fluid from the distal portion of main lumen 18 to the proximal portion of main lumen 18.

Figure 5:
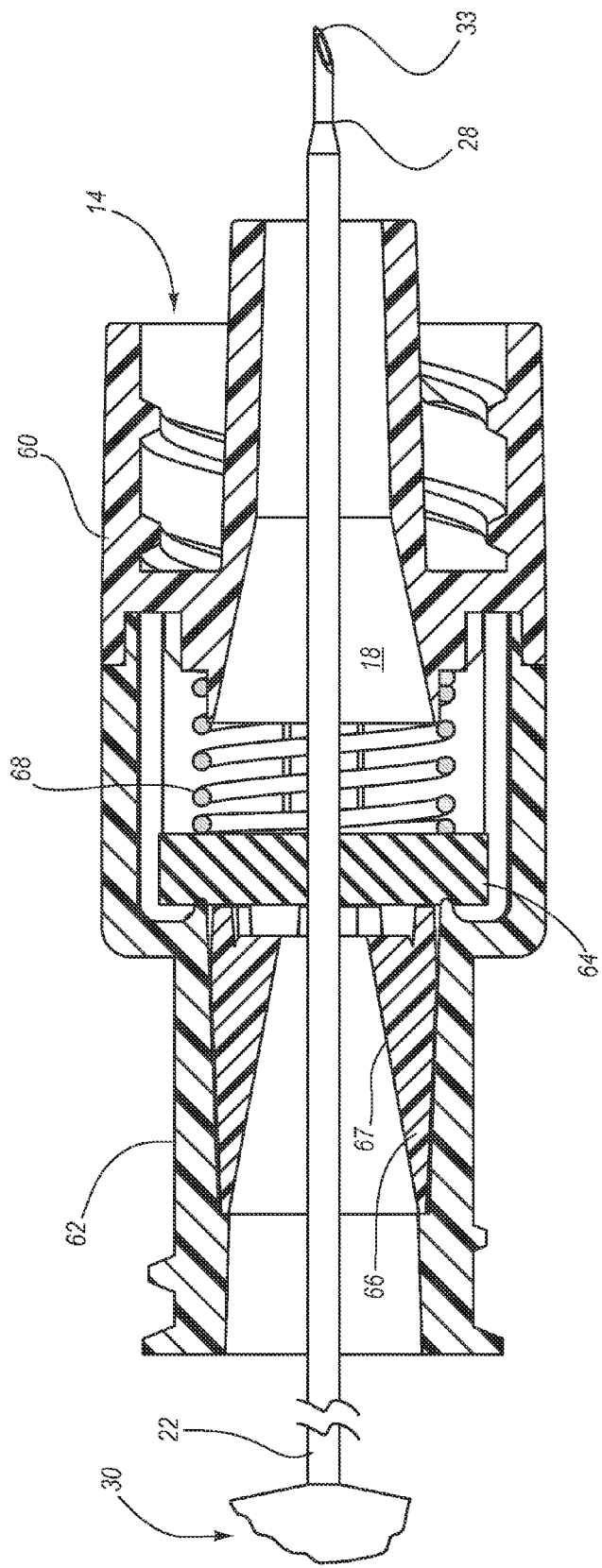
FIG. 5 is a cross-sectional side view of the valved connector illustrating the manner in which a needle, catheter or cannula can cause opening of the seal of the valved connector.

FIG. 5 is a cross-sectional view of valved connector 10 illustrating the manner in which a needle 30 can be utilized to permit the passage of fluid through seal 64. In the illustrated embodiment, a needle cannula has been advanced through main lumen 18 of valved connector 10 such that a needle cannula 32 is positioned through the middle of seal 64. Lumen 36 is positioned through the middle of needle 30 allowing the passage of fluid from the distal end of valved connector 10 to the proximal end of valved connector 10, thereby facilitating the passage of fluids through valved connector 10.

According to one embodiment of the present invention, the seal of valved connector includes crisscross bicuspid-type slits, which permit the passage of a needle, cannula, or a guide wire through the middle of valved connector. In another embodiment, the material properties permit the passage of a needle through valve, while providing desired resealing upon the removal of the needle through valve. In yet another embodiment, a combination of the material properties and slit configuration can be utilized without departing from the scope and spirit of the present invention. As can be seen, the configuration of seal engagement apparatus 66 is configured such that the sloping of tapered surface 67 permits the passage of smaller instruments, such as a needle, or guide wire, through the middle of main lumen without obstruction and without resulting in lateral displacement of seal engagement apparatus 66. In this manner, both a smaller diameter apparatus, such as needle 30 or a guide wire, can be passed through seal 64, or alternatively, a larger connector, such as that with apparatus 50 shown in FIG. 4, can be utilized to permit the passage of fluids through valved connector 10.

Figure 6A:
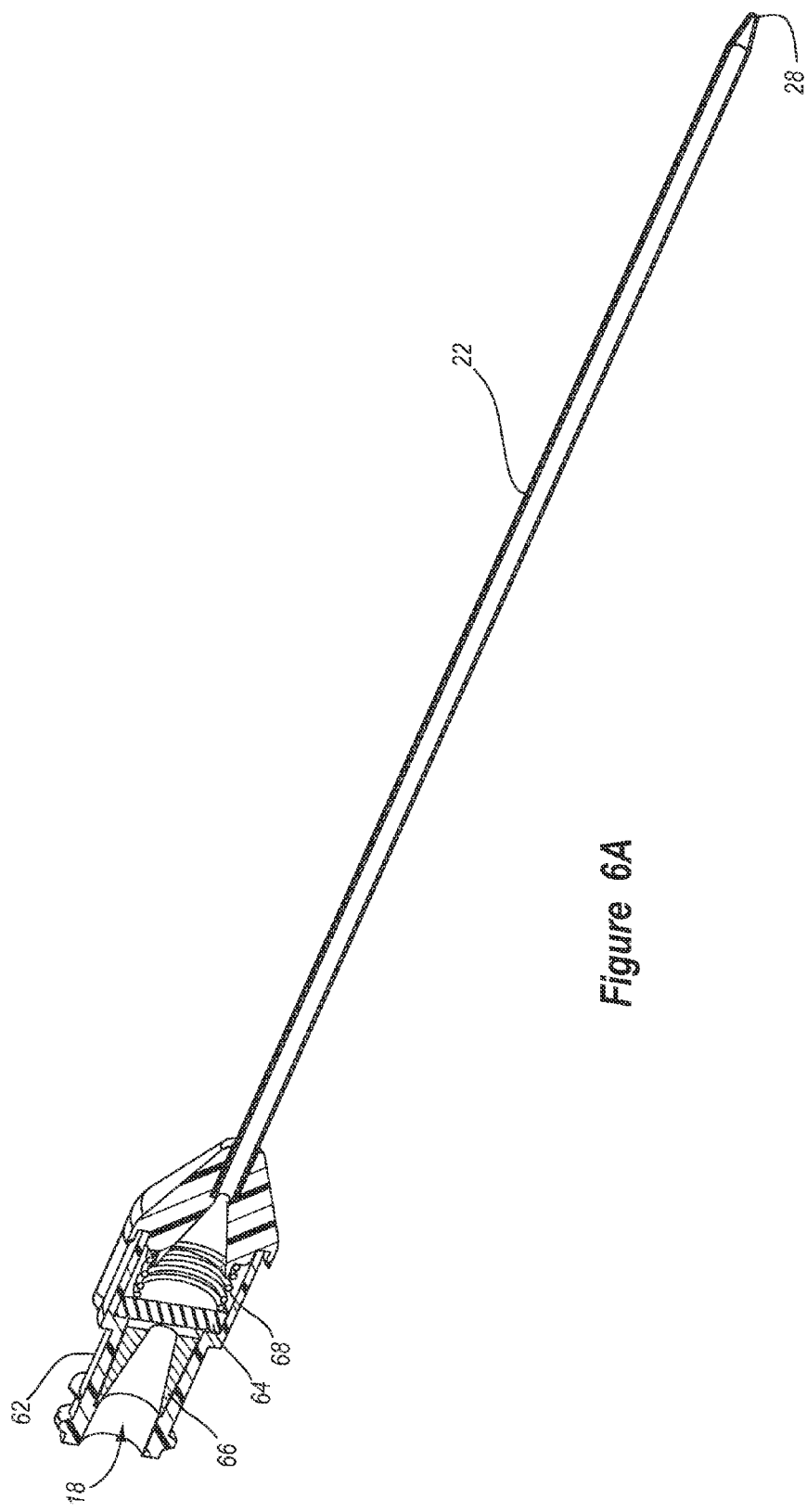
FIG. 6A is a cross-sectional perspective view of an integral component having a valved hemostasis seal component according to one aspect of the present invention.

FIG. 6A is a perspective view of a valved apparatus in which a catheter, needle, or trocar is integrally coupled to a valved connector. In other words, the hub of the access apparatus includes internal components which allow the use of an apparatus connector or a needle or other apparatus to open the seal associated with the hub. In the illustrated embodiment, an integral component is provided. Integral component includes a proximal end 18 and a distal end 28. In the illustrated embodiment, proximal end 18 comprises a threaded coupler and the distal end includes a catheter apparatus 28. A hub 106 is positioned between proximal end 102 and distal end 104. Hub 62 includes internal components which are similar in operation and function to valved connector 10 of FIGS. 1A through 5. In the illustrated embodiment, the internal components of hub 62 comprise a seal engagement apparatus 66, a seal 64, and a spring 68. When an engagement apparatus is positioned in cooperative communication with the proximal end 18 of integral component, seal engagement apparatus 66 is moved in an axial direction which overcomes the forces of spring 68. In this manner, seal 64 can be moved distally, permitting the passage of fluids through a main lumen 22 of integral component 100. Alternatively, a needle, trocar, guide wire, or other device can be advanced through the middle of seal 64.

Figure 6B:
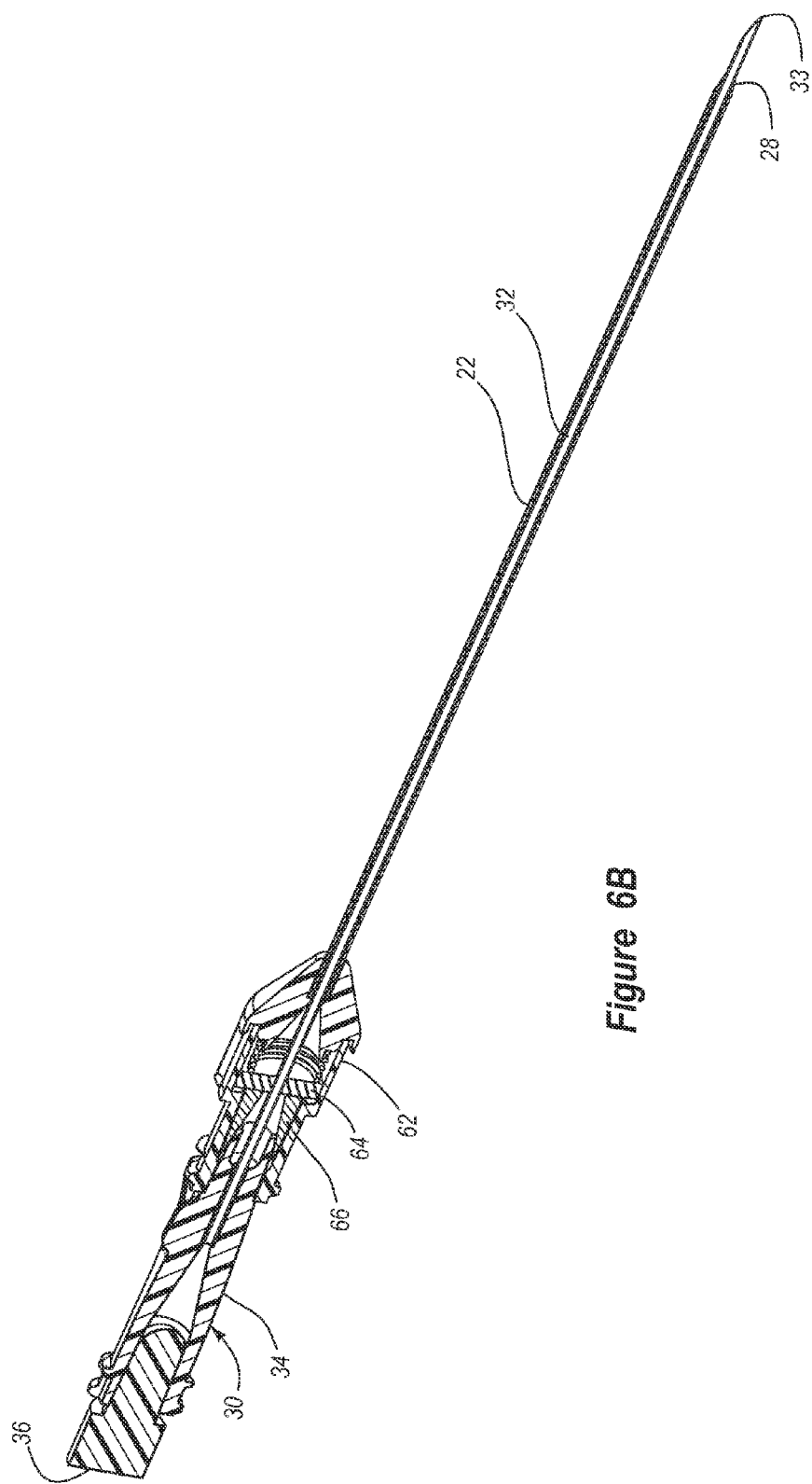
FIG. 6B is a cross-sectional perspective view of a integral component of FIG. 6A illustrating the use of a needle apparatus according to one aspect of the present invention.

FIG. 6B illustrates the insertion of a needle apparatus. Needle apparatus can provide sufficient rigidity to the distal end of integral component to allow insertion of the distal end of integral component into a desired position within a patient. In the illustrated embodiment, the needle of the needle apparatus is positioned through the middle of seal 64. Additionally, a component of the hub of the needle apparatus engages the seal engagement apparatus 66, causing movement of the seal 64 while also allowing the passage of fluids around the external portion of seal 64.

FIG. 7A is a side view of a valved connector 100 according to one embodiment of the present invention. In the illustrated embodiment, valved connector 100 is adapted to be utilized with a catheter or other instrument. The volume of fluid can be a volume of urine within the patient's bladder or other urinary tract location, blood from the patient's vasculature, or any other area where fluid is positioned within the patient. In some embodiments, the volume of fluid is not desired to be drained but rather retained within the patient and the valve apparatus is adapted to allow desired instruments or other procedures to be performed in a largely bloodless and hemostatic manner.

In the illustrated embodiment, valved connector 100 comprises a distal body component 110 and a proximal body component 112. Proximal body component 112 includes threads 114 and collar 116. Distal body component 110 includes taper 120 at distal tip 118, threads 122 and extension section 124. In the embodiment, distal body component 110 is connected to a catheter, or other access device inserted into the patient. Threads 114 comprise a luer connector 114 which can be utilized to secure additional medical devices or components to valved connector 100.

Collar 116 is positioned as a rim or stop against which threaded components abut to control advancement of threaded coupling components beyond their intended threaded advancement. Threads 122 have a smaller thread displacement than threads 114. Threads 122 can provide a long term secure coupling to the apparatus to which valved connector 100 is secured. Taper 120 of distal tip 118 provides a mechanism to provide simple and efficient insertion of distal tip 118 into a female coupling member during securement of valved connector 100 to tubing, a connector or another medical apparatus. Extension section 124 is positioned between collar 116 and threads 122. Extension section 124 provides displacement to ensure desired coupling of valved connector 100 to a secondary apparatus. According to one aspect of the present invention, extension section 124 can allow a desired length of distal body component 110 while minimizing the total length of threads 122.

As will be appreciated by those skilled in the art, a variety of types and configurations of valved connectors can be provided without departing from the scope and spirit of the present invention. For example, in one embodiment, the threads on the proximal body component have the same displacement as the threads on the distal body component. In another embodiment, one or both of the threads are provided in a female configuration rather than a male configuration.

FIG. 7B illustrates a cross-sectional side view of valved connector 100 according to one embodiment of the present invention. In the illustrated embodiment, valve 126 is secured relative to the other components of valved connector 100 by a securement flange 132 of a cap member 130. Valve member 126 includes a securement flange 128 on its outside diameter. Securement flange 128 is secured cap member flange 132 and valve securement portion 134. Cap member 130 slides over valve securement portion 134 such that valve securement portion 134 comprises a male member which fits inside and contacts the inside diameter of valve securement portion 134. Distal portion 136 of cap member 130 contacts a proximal portion 138 of collar 116. In this manner, desired securement of cap member 130 relative to proximal body component is provided while also securing valve 126.

A main lumen 140 is positioned along the length of valved connector 100. Main lumen 140 includes a valve chamber 142, a tapered portion 144 and a distal lumen portion 146. Valve 126 is configured to allow a medical instrument, needle or dilator to pass from the external environment into main lumen 140 while maintaining hemostasis within main lumen 140. In the event that the apparatus which opens valve 126 comprises a dilator which is intended to provide open and ongoing flow from main lumen 140, through the dilator and into a secondary medical instrument, such dilators can be secured in threaded relationship to threads 114. The size and shape of such dilators can be received within the enlarged valve chamber 140 without obstruction or damage to valved connector 100. In the event a needle, guidewire or other instrument is provided to pass along the entire length of main lumen 140, the instrument can pass through valve chamber 142 and then be directed into the smaller diameter of distal lumen portion 146 by tapered portion 144.

One of the benefits of utilizing a valved connector 100 is that valved connector 100 is adapted to allow a needle, cannula, or other implement to be passed through main lumen 18. The configuration of the valved connector 100 allows not only the passage of the instrument, but also the passage of fluid through the needle permitting the passage of fluid from the distal end of valved connector 10 to the proximal end of valved connector 10. Additionally, in longer term applications, such as dialysis or drainage devices, valved connector 100 can be removed and replaced with a new valved connector to maintain and ensure a sterile environment, continued desired operability of the valved connector 100 or to replace a damaged or worn out valved connector 100.

As will be appreciated by those skilled in the art, a variety of types and configurations of valved connectors can be utilized within the scope and spirit of the present invention without departing from the scope and spirit of the present invention. For example, in one embodiment, the valved connector can be configured for use in connection with one or more of drainage catheter, an IV catheter, a dialysis catheter, an IV set, an IV introducer needle or other illustrative medical apparatus and applications.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A valved connector configured to selectively permit a passage of fluid, the valved connector comprising:
   a body member having a proximal end defining a proximal-facing surface and a distal end;
   a valve having a proximal surface and a distal surface, the valve disposed such that a perimeter of the proximal surface of the valve is flush with the proximal-facing surface of the body member along a plane that is orthogonal to a longitudinal axis of the body member;
   a lumen having a proximal end, a distal end, and a tapered lumen portion, the lumen disposed within at least a portion of the body member distal to the distal surface of the valve, the lumen configured to provide fluid communication between the distal surface of the valve and the distal end of the body member; and
   a first set of threads having a proximal end and a distal end, the proximal end of the first set of threads disposed adjacent the proximal end of the body member and the first set of threads extending distally around a portion of an outer diameter of the body member;
   wherein the proximal end of the first set of threads is disposed flush with the proximal surface of the valve, and wherein the valve is configured to allow fluid to pass through the lumen when a secondary device is coupled to the first set of threads.

2. The valved connector of claim 1, wherein the body member comprises a proximal body component and a distal body component, and wherein the distal body component comprises a taper configured to facilitate coupling of the distal body component to another device.

3. The valved connector of claim 2, wherein the proximal body component comprises the first set of threads and the distal body component comprises a second set of threads.

4. The valved connector of claim 1, wherein the valve is configured to open when a luer connector is coupled to the first set of threads.

5. The valved connector of claim 1, wherein the valve is configured to allow passage of an elongate instrument through the valve, while maintaining hemostasis within the lumen.

6. The valved connector of claim 1, wherein the tapered lumen portion is configured to direct the insertion of an elongate instrument through the valved connector.

7. The valved connector of claim 1, wherein the body member comprises a body securement flange configured to retain the valve.

8. The valved connector of claim 7, wherein the valve comprises a valve securement flange configured to contact the body securement flange.

9. The valved connector of claim 8, wherein the body member comprises a proximal body component and a distal body component, the proximal body component comprising the body securement flange, and wherein the valve securement flange is disposed between the body securement flange and a proximal end of the distal body component.

10. The valved connector of claim 1, wherein the distal surface of the valve is curved toward the proximal surface of the valve.

11. A valved connector configured to selectively permit a passage of fluid, the valved connector comprising:
    a body member comprising a proximal end defining a proximal-facing surface, a distal end, and a body securement flange disposed adjacent the proximal end of the body member;
    a valve having a proximal surface and a distal surface, the valve disposed within the body member such that a perimeter of the proximal surface of the valve is flush with the proximal-facing surface of the body member along a plane that is orthogonal to a longitudinal axis of the body member;
    a lumen disposed within at least a portion of the body member such that the distal surface of the valve is disposed at a proximal end of the lumen, the lumen configured to provide fluid communication between the distal surface of the valve and the distal end of the body member; and a first set of threads comprising a proximal end and a distal end, the proximal end of the first set of threads disposed adjacent the proximal end of the body member and the first set of threads extending distally from adjacent the proximal end of the body member around an outer diameter of the body member;

wherein the proximal end of the first set of threads is disposed flush with the proximal surface of the valve; and wherein the body securement flange is configured to retain the valve within the lumen of the body member.

12. The valved connector of claim 11, wherein the lumen comprises a tapered lumen portion configured to direct the passage of an elongate instrument through the valved connector.

13. The valved connector of claim 11, wherein the body member comprises a proximal body component and a distal body component, the proximal body component comprising the first set of threads.

14. The valved connector of claim 13, wherein the valve is configured to allow fluid communication between a luer connector coupled to the first set of threads and the lumen while sealing the lumen from the exterior environment.

15. The valved connector of claim 13, wherein the distal body component comprises a taper configured to facilitate coupling of the distal body component to another device.

16. The valved connector of claim 15, wherein the distal body component comprises a second set of threads.

17. The valved connector of claim 11, wherein the valve comprises a valve securement flange adjacent the body securement flange.

* * * * *